United States Patent [19]

Pfeifer

[11] Patent Number: 5,065,657

[45] Date of Patent: Nov. 19, 1991

[54] AUTOMATIC LOCKING MECHANISM FOR THE DRIVE DEVICE OF A MICROTOME

[75] Inventor: Gerhard Pfeifer, Solms, Fed. Rep. of Germany

[73] Assignee: Wild Leitz GmbH, Wetzlar, Fed. Rep. of Germany

[21] Appl. No.: 401,765

[22] Filed: Sep. 1, 1989

[30] Foreign Application Priority Data

Sep. 9, 1988 [DE] Fed. Rep. of Germany ....... 3830725

[51] Int. Cl.⁵ .............................................. G01N 1/06
[52] U.S. Cl. ..................................... 83/703; 83/718; 83/915.5; 83/DIG. 1
[58] Field of Search .................... 83/703, 715–718, 83/729, 730, DIG. 1, 915.5

[56] References Cited

U.S. PATENT DOCUMENTS

| | | | |
|---|---|---|---|
| 3,191,477 | 6/1965 | Danon | 83/915.5 |
| 3,491,638 | 1/1970 | Idlis | 83/915.5 |
| 4,479,402 | 10/1984 | Reichel et al. | 83/915.5 |
| 4,598,621 | 7/1986 | Weinhold | 83/915.5 |

OTHER PUBLICATIONS

"Leitz 1512 Rotary Microtome", Apr. 1981, pp. 1–12. Ernst Lietz Wetzlar GmbH, Germany.

*Primary Examiner*—Hien H. Phan
*Attorney, Agent, or Firm*—Foley & Lardner

[57] ABSTRACT

A microtome with a drive device is described, which has a shaft and a handwheel, arranged thereupon, with a grip. For locking the drive device, an electromagnet is firmly arranged on the housing frame of the microtome. The latter is in effective connection with an indexing ring, axially displaceable on the shaft. A control device, which is electrically connected to the electromagnet and to a sensor, controls the electromagnet in response to a signal of the sensor. The sensor triggers the signal by the position of an indexing ring arranged axially displaceably on the shaft. The said indexing ring is movable in frictional connection with a pin arranged in the grip and axially displaceable by means of a lever. The lever is actuated by seizing of the grip and the locking of the drive device is cancelled.

18 Claims, 4 Drawing Sheets

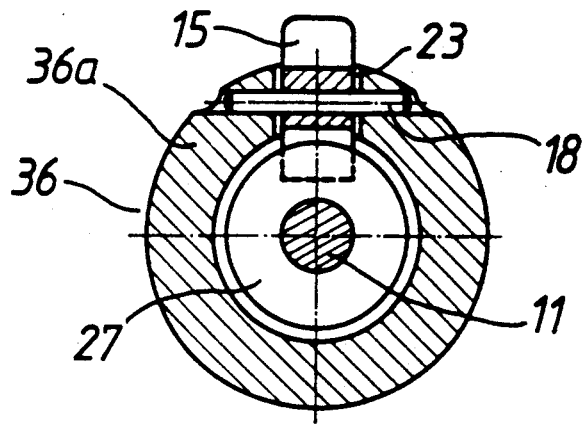
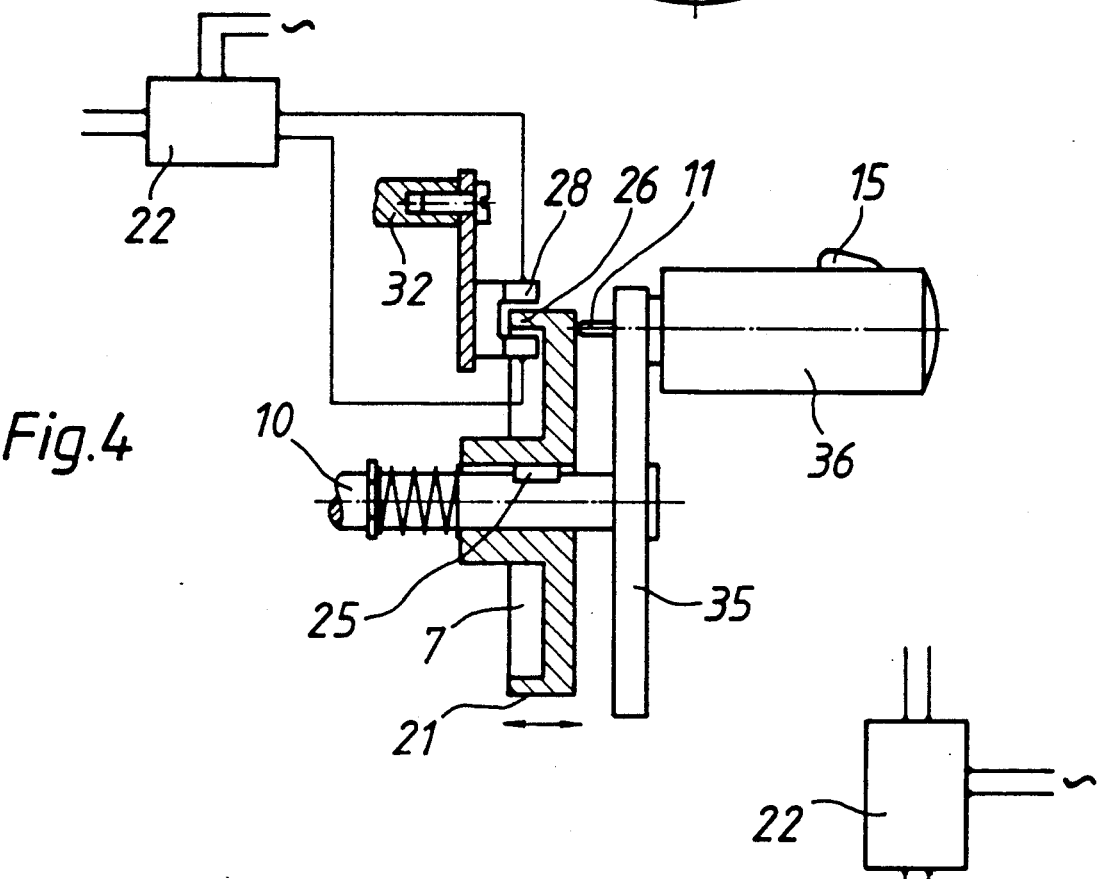
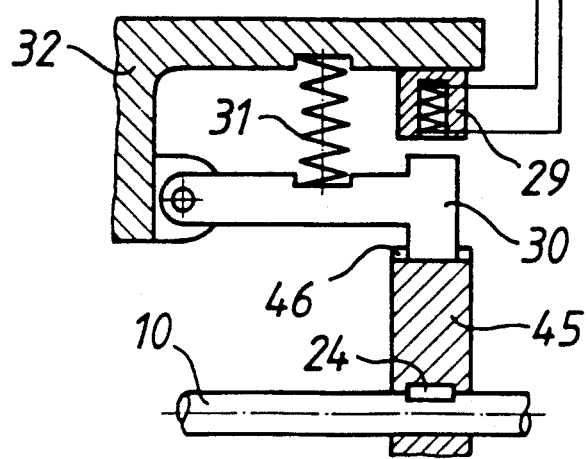

AUTOMATIC LOCKING MECHANISM FOR THE DRIVE DEVICE OF A MICROTOME

BACKGROUND OF THE INVENTION

The invention relates to an automatic locking of the drive device of a microtome actuated by a handle.

Known microtomes with a handle for the manual actuation of the drive device for the cutting operation have a safety device for blocking the handle. This is essential in order to rule out the risk of injury by an unintentional movement of the object holder or of the cutting knife when changing the object to be cut or when changing or aligning the cutting knife. It is therefore usual to lock the handle by a clamping lever arranged in the vicinity of the handle. However, this presupposes that the operator deliberately actuates this safety device. Operating errors are possible due to this laborious handling and consequently the risk of a considerable injury on the cutting knife is not to be ruled out.

SUMMARY OF THE INVENTION

It is the object of the present invention to increase the operational safety of a microtome in an ergonomically advantageous way in order to rule out the risk of injury by maloperation.

This object is achieved according to the invention by providing a microtome comprising a drive device for producing a movement between a knife and an object holder; and a blocking mechanism for locking the drive device, wherein the handle comprises switching means for actuation of the blocking mechanism.

BRIEF DESCRIPTION OF THE DRAWINGS

The invention is represented diagrammatically in a number of exemplary embodiments in the drawing, in which:

FIG. 3 shows a section through the handle of the microtome along the line I—I,

FIG. 4 shows an exemplary embodiment with a light barrier,

FIG. 5 shows a further exemplary embodiment with an electromagnet,

DETAILED DESCRIPTION OF THE PREFERRED EMBODIMENTS

Figure 1:
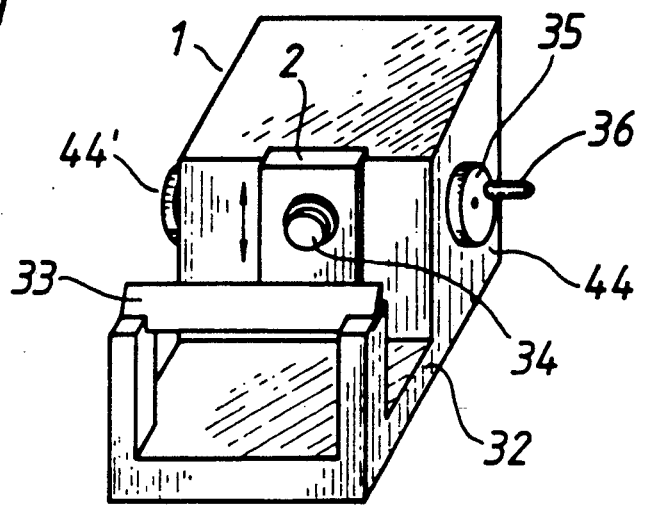
FIG. 1 shows an overall view of a rotational microtome.

FIG. 1 diagrammatically shows a rotational microtome 1 according to the invention, with a housing frame 32, a stationary knife 33, and an object carriage 2, movable in arrow direction, on which an object holder 34 is arranged. A handle 44 with a handwheel 35 and a grip 36 are used for the manual drive of the object carriage 2. A further handle 44' is arranged opposite the handle 44 on the microtome 1 for the manual drive of the object carriage 2.

Figure 2:
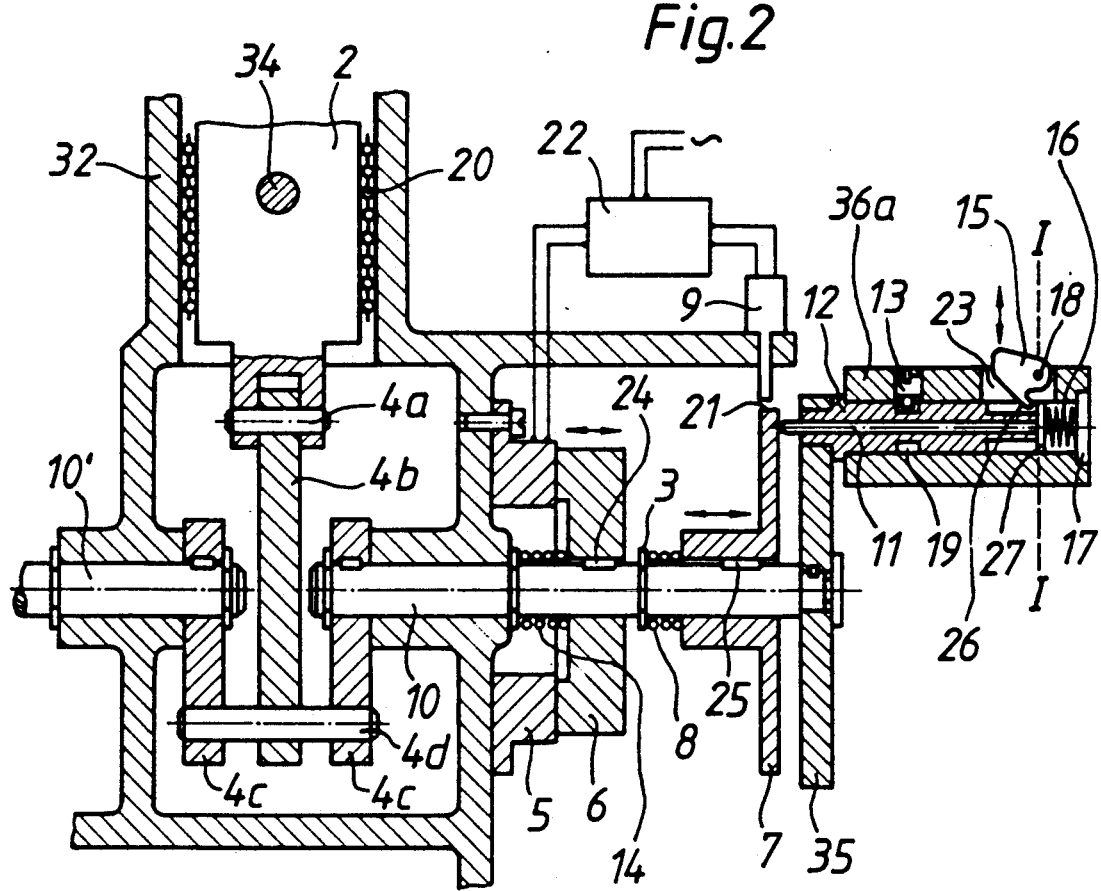
FIG. 2 shows a section through the microtome.

In FIG. 2, a section through the microtome 1 is represented. The object carriage 2 with the object holder 34 is movably mounted on the housing frame 32 via a roller guide 20 and connected to a shaft 10 via conventional mechanical coupling elements, spindle journal 4a, connecting rod 4b, thrust crank 4c and spindle journal 4d. The shaft 10 is fastened rotationally movably on the housing frame 32 and has at its end the handle 44 for driving the object carriage 2. The shaft 10 is surrounded by an electromagnet 5, firmly fastened on the housing frame 32. The electromagnet is designed here as an electro-permanent magnet, i.e. in the permanent magnet there is provided a coil, which cancels the permanently acting magnetic forces by applying an electric voltage.

As counterpart to this magnet, a clutch disk 6 is arranged on the shaft 10 in a way secured against rotation by means of a fitted key 24 and is designed axially displaceably with a compression spring 14. The range of this movement is limited by a locking washer 3 firmly arranged on the shaft 10. A further indexing ring 7, arranged on the shaft 10 and axially displaceable with a compression spring 8, is likewise fastened on the shaft 10 in a way secured against rotation by means of a fitted key 25.

The shaft 10 is connected via the coupling element 4d to a further shaft 10', which likewise has a safety device (not shown) and is in effective connection with the handle 44'.

Furthermore, FIG. 2 shows a control device 22, which is electrically connected to a sensor 9, fastened on the housing frame 32 and opposite the indexing ring 7, as well as to the electromagnet 5.

The grip 36, arranged on the handwheel 35, has a gripping piece 36a, shaped as a sleeve, which is rotationally movable freely about the spindle 12 of the grip 36, but secured against an axial displacement. For this purpose, the spindle 12 has an annular groove 19, into which a threaded pin 13 engages. Inside the spindle 12, an axially displaceable pin 11 is arranged, the end of which is in effective frictional connection with the indexing ring 7. Inside the grip 36, the pin 11 is assigned a round disk 27, on which a further compression spring 16 is supported. The second stop surface for the compression spring 16 is formed by a plug 17 screwed into the grip 36. The gripping piece 36a has a relief 23, from which a lever 15 projects. The latter is secured by means of a pin 18 and movable in arrow direction. Its end in the grip is in frictional connection with the disk 27.

The manual microtome drive represented here is put in operation by turning of the handwheel 35. In this case, the shaft 10 is turned by means of the grip 36 The coupling elements 4a to 4d arranged on the shaft transfer the movement to the object carriage 2. In this case, the rotational movement of the shaft 10 is converted in the manner of a thrust crank drive into an oscillating linear movement. The safety device of the microtome 1 must in this case be put out of operation. This is performed by the lever 15 being pressed into the grip 36 by the seizing of the gripping piece 36a, and the disk 27 moved against the force of the compression spring 16 in the direction of the plug 17. Due to the connection of the disk 27 to the pin 11, the latter is drawn back into the grip 36 and the frictional connection of pin 11 and indexing ring 7 is cancelled. Due to the force of the compression spring 8, the indexing ring follows the movement of the pin 11.

In this case, the edge 21 of the indexing ring 7 leaves the operating range of the sensor 9, which is designed here as a proximity sensor. The sensor emits an electric signal to the control device 22, which applies current to the electromagnet 5. As a result, the permanent magnet coupling between the electromagnet 5 and the clutch disk 6 is cancelled, since the magnetic forces between the electromagnet 5 and the clutch disk 6 are smaller than the force of the compression spring 14, the clutch disk 6, secured against rotation on the shaft 10 and axially displaceable, being pressed against the locking washer 3. The decoupling of the electromagnet 5 from the clutch disk 6 consequently cancels the blocking of the shaft 10. By releasing the grip 36, the pin 11 is moved by means of the force of the spring 16 against the indexing ring 7 and the latter is moved with its edge 21 into the operating range of the sensor 9. In this case, the compression spring 8 is tensioned, the force of which is of course smaller than the force of the spring 16 in the grip 36. Due to the approach of the indexing ring 7, the sensor 9 emits a corresponding signal to the control device 22, which interrupts the current to the electromagnet 5. The magnetic forces between the clutch disk 6 and the electromagnet 5 are now greater again than the force of the compression spring 14. This results in a frictional connection of clutch disk 6 and the electromagnet 5 and thus in a blocking of the shaft 10.

FIG. 3 shows a section along the line I—I from FIG. 2. The section represented through the grip 36 shows the outer, rotatable gripping piece 36a and the inner disk 27 with the pin 11 located thereupon. The lever 15, projecting with one end out of the gripping piece 36a, is mounted pivotally in the gripping piece 36a by means of the locking pin 18.

The inner end of the lever 15 is in frictional connection (spring 16 from FIG. 2 is not shown here) with the disk 27. The effective connection of the lever 15 with the disk 27 is thus independent of a rotation of the gripping piece 36a about the pin 11 or the spindle 12.

FIG. 4 shows a variant of the version of the sensor 9 from FIG. 2. The sensor is designed here as a light barrier 28 and is connected via electric leads to the control device 22. A fin 26 arranged on the indexing ring edge 21 of the ring 7 projects into the U-shaped profile of the light barrier 28. The fin 26 is of annular design, so that it embraces the entire circumference of the indexing ring 7. As already stated with respect to FIG. 2, the indexing ring 7 is designed axially displaceably on the shaft 10 in dependence on the pin 11, whereby the fin 26 initiates the switching contact of the light barrier 28. The electromagnetic clutch is actuated via the control device 22.

In FIG. 5, a variant of the blocking of the shaft 10 is shown. The electric permanent magnet clutch represented in FIG. 2 with the electromagnet 5 and the clutch disk 6 is replaced here by a blocking disk 45 arranged firmly on the shaft 10. This disk 45 has on its outer circumference a gear ring 46, into which a lever 30, pivotally fastened on the housing frame 32, engages. Between this lever 30 and the housing frame 32 there are arranged a compression spring 31 and an electromagnet 29. The latter is electrically connected to the control device 22, already described.

If the control device 22 has a corresponding signal of the sensors, already described, applied to it, it emits a corresponding signal to the electromagnet 29. The magnetic force, which is of course greater than the force of the spring 31, lifts the lever 30 out of its effective connection with the gear ring 46. By disconnecting the electromagnet 29, the lever 30 is brought by means of the force of the spring 31 back into effective position with the gear ring 46 of the blocking disk 45 and thus locks the shaft 10.

Figure 6:
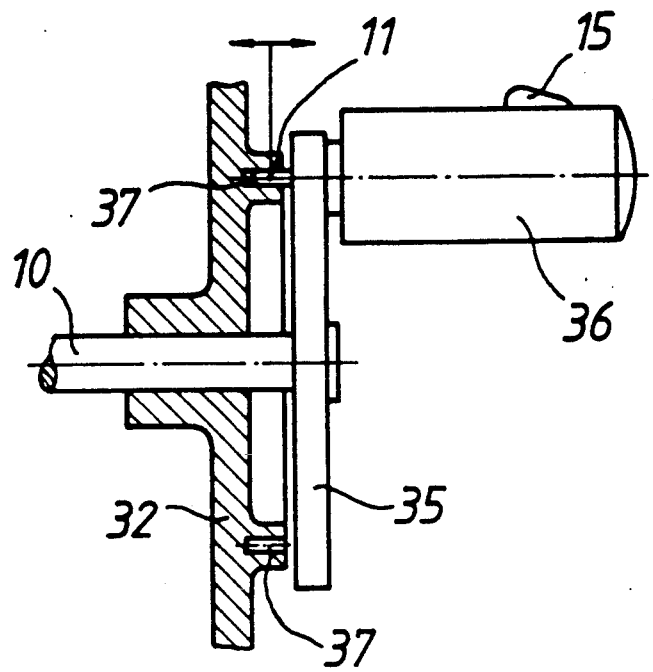
FIG. 6 shows the handle of the microtome with a latching mechanism.

FIG. 6 shows a purely mechanically operating variant of the blocking mechanism. In the housing frame 32, for this individual reliefs 37, arranged next to one another, are provided on a circular track. The reliefs 37 are dimensioned in such a way that the pin 11 engages in them. The pin 11 is in this case, as already described in FIG. 2, made axially displaceable in the grip 36 by means of the lever 15.

Figure 7:
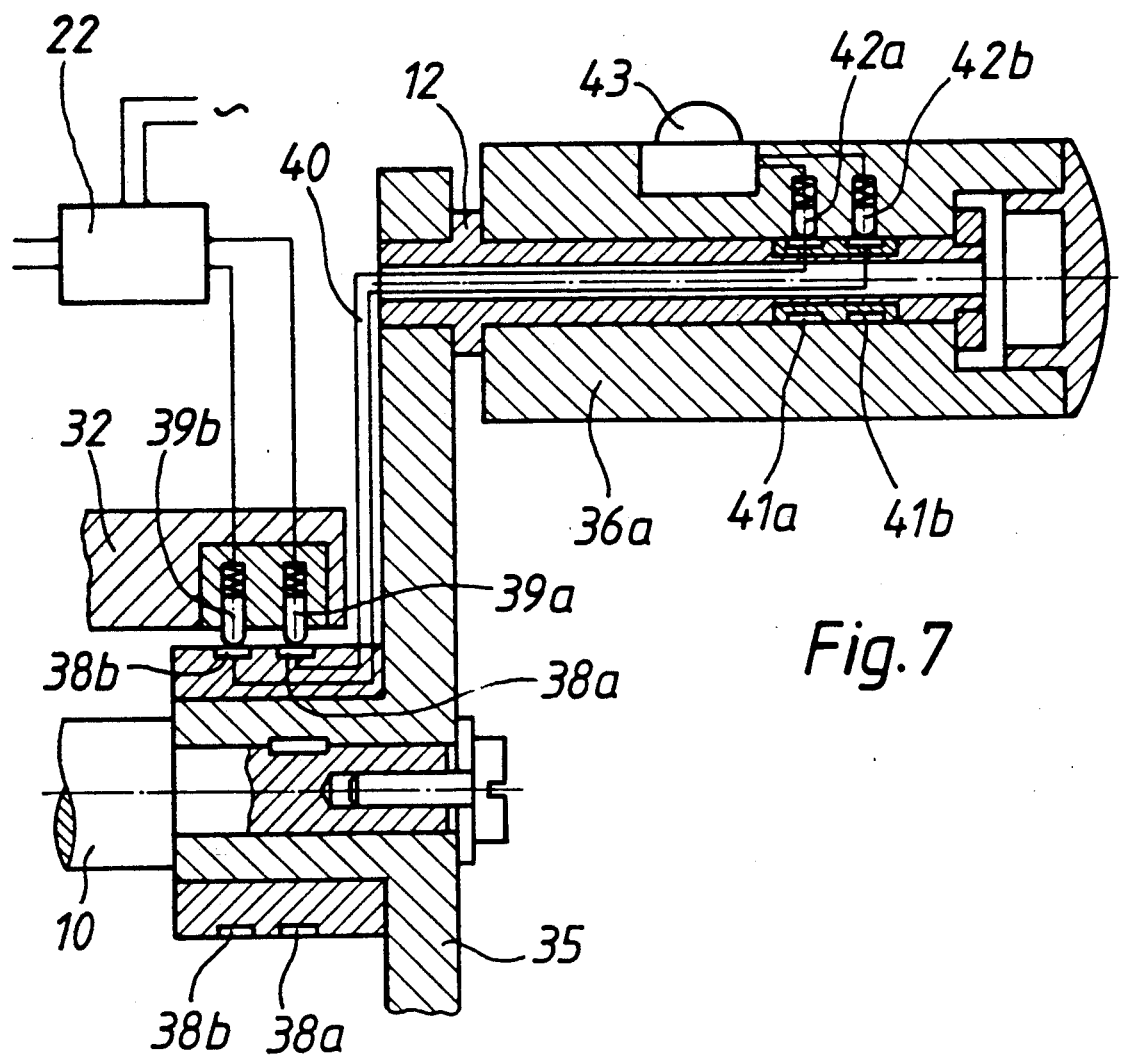
FIG. 7 shows a further exemplary embodiment of the handle with an electric switch.

In FIG. 7, an electrically operating actuation device for the blocking mechanism is represented diagrammatically. In the rotatable gripping piece 36a, for this there is arranged a switch 43, which is electrically connected to two sliding contacts 42a and 42b. The spindle 12 of the grip 36, rigidly arranged on the handwheel 35, has a sliding track 41a and 41b in each case opposite the sliding contacts 42a and 42b. The said tracks are each connected via electric leads 40 to a further sliding track 38a and 38b, arranged on the handwheel 35. The latter tracks are each assigned a further sliding contact 39a and 39b opposite them. Both are firmly arranged in the housing frame 32 of the microtome 1 and electrically connected to the control device 22. By actuation of the switch 43 in the gripping piece 36a, a corresponding electric signal is triggered in the control device 22.

Figure 8:
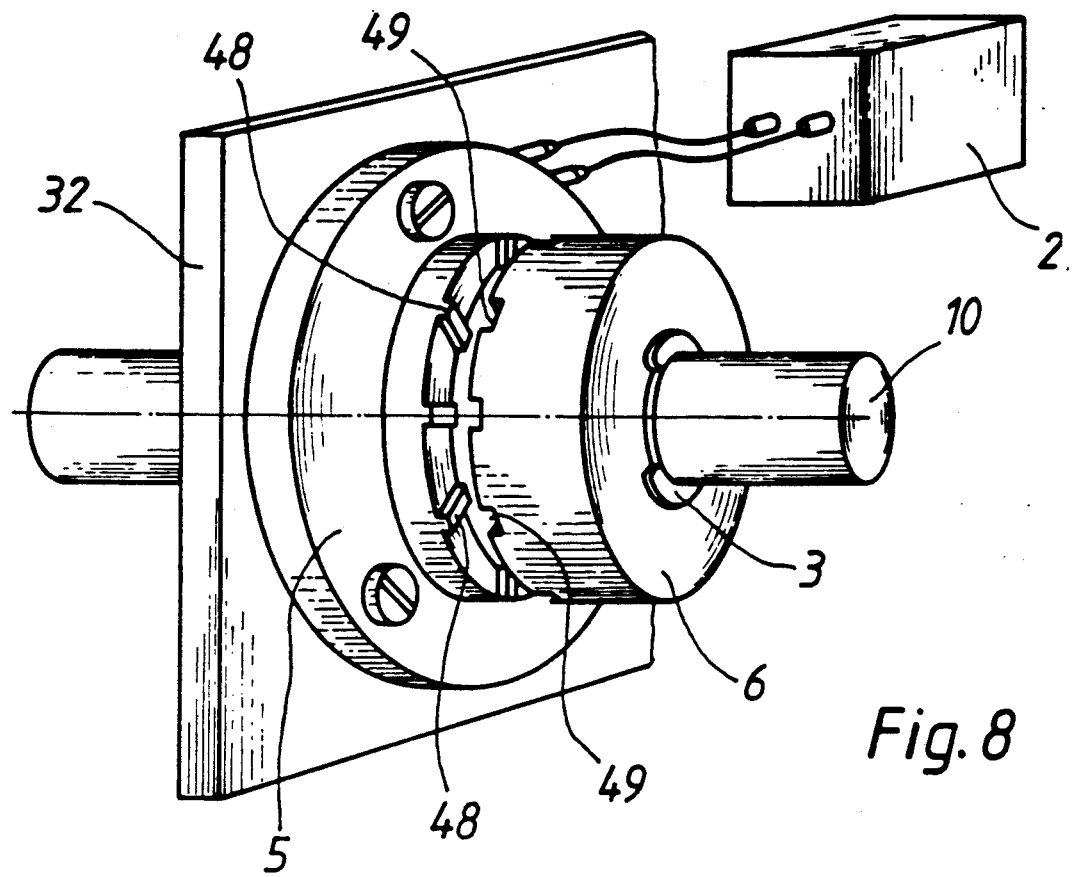
FIG. 8 shows a magnetic clutch with a toothing.

FIG. 8 shows a cut-out from FIG. 2 with the electropermanent magnet 5, which is firmly connected to the housing frame 32 and connected via electric leads to the control device 22. Arranged axially displaceably opposite it on the shaft 10 is the clutch disk 6. The magnet 5 has a plurality of latching lugs 48, the counterparts of which are provided as latching grooves 49 on the clutch disk 6. If the latching lugs 48 engage in the latching grooves 49, as well as the frictional connection by the magnetic forces, a positive connection of the clutch disk 6 to the magnet 5 is achieved, and thus a still more effective locking of the shaft 10.

Figure 9:
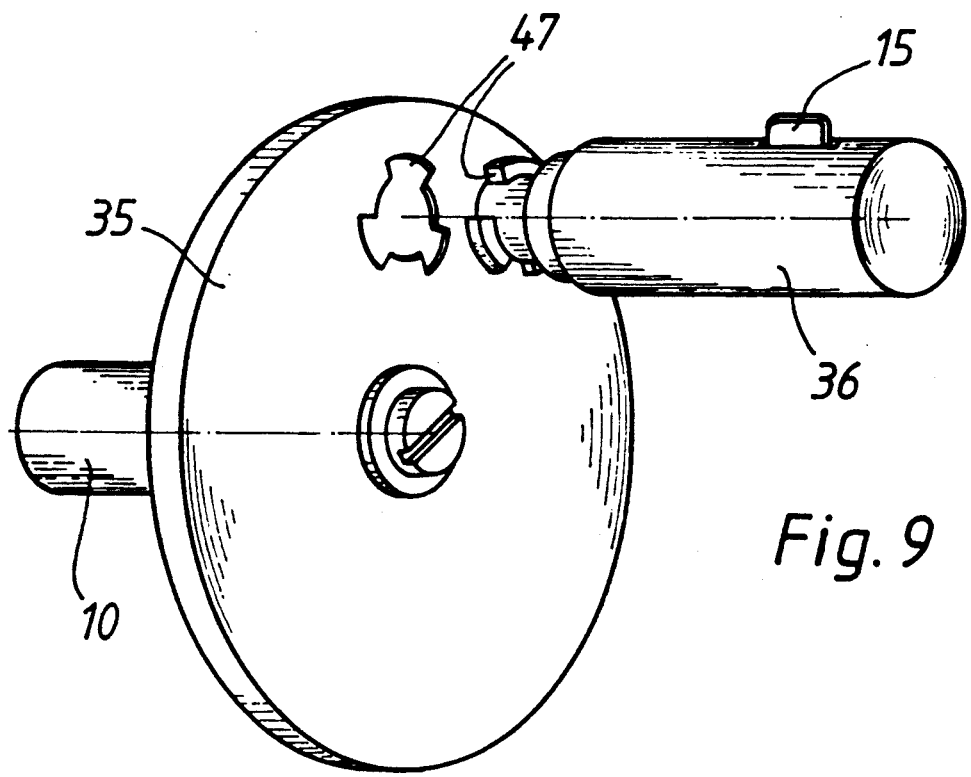
FIG. 9 shows a handwheel with a grip detachably fastened thereupon.

In FIG. 9, the handwheel 35 is represented, with the shaft 10 arranged thereupon and the grip 36. For the detachable fastening of the grip 36, a coupling 47, designed here as bayonet, is provided between it and the handwheel 35. This coupling 47 is of particular advantage especially whenever the microtome has a further handle 44' for the manual drive of the object carriage 2. In this case, as already indicated in FIG. 2 with the shaft 10', of course the necessary transfer elements (7, 9; 7, 26, 29; 37; 38a–40) are arranged on both sides in and on the microtome, so that here too the safety device is fully effective.

The safety device according to the invention, which has been described with reference to exemplary embodiments on a rotational microtome, increases the operational safety of such a unit with ergonomically better arrangement of the actuating elements. Since the drive device is locked immediately after release of the grip, uncontrolled movements of the object carriage or of the knife, and the associated risk of injury, are ruled out.

Of course, the safety device can also be provided on a base-carriage microtome. It is also possible to use a simple electromagnet instead of the electro-permanent magnet described. In this case, however, it must be taken into consideration that the safety device is only effective when the voltage source is connected.

The foregoing description and examples have been set forth merely to illustrate the invention and are not intended to be limiting. Since modifications of the disclosed embodiments, incorporating the spirit and substance of the invention may occur to persons skilled in the art, the scope of the invention should be limited solely with reference to the appended claims and equivalents.

What is claimed is:

1. A microtome comprising:
   a drive device for producing a movement between a knife and an object holder;
   a first handle having a gripping surface for an operator, for manual actuation of the drive device;
   a blocking mechanism for locking the drive device, thereby preventing motion of the handle and the object holder;
   switching means associated with the gripping surface of the handle for actuating the blocking mechanism whenever an operator releases his hand from the gripping surface; and
   a second handle having a gripping surface for an operator, for manual actuation of the drive device, said second handle being mounted on a side of the microtome opposite the first handle, and the second handle also including switching means associated with its gripping surface for actuating the blocking mechanism whenever an operator releases his hand from its gripping surface, and wherein the gripping surfaces of the first and second handles are detachably connected to the handles, whereby a single gripping surface can be interchangeably used on both of the first and second handles for selective right-hand or left-hand operation.

2. The microtome as claimed in claim 1, wherein the blocking mechanism comprises an electromagnet, arranged in the microtome, and a disk rotationally fixedly mounted on a shaft of the drive device.

3. The microtome as claimed in claim 2, wherein the disk comprises a gear ring, and said blocking mechanism includes a blocking lever, pivotally arranged on a housing frame of the microtome for engagement with said gear ring responsive to the electromagnet.

4. The microtome as claimed in claim 2, wherein the electromagnet is arranged on a housing frame, comprises an annular electro-permanent magnet, and is arranged opposite the disk, which is mounted axially displaceably on the shaft.

5. The microtome as claimed in claim 4, wherein the electromagnet and the disk comprise toothing.

6. The microtome as claimed in claim 2, further comprising a control device electrically connected to the electromagnet and to a sensor.

7. The microtome as claimed in claim 6, wherein the sensor comprises a proximity sensor for detecting the position of an axially displaceable indexing ring rotationally fixedly mounted on the shaft.

8. The microtome as claimed in claim 6, wherein the sensor comprises a light barrier for detecting the position of an axially displaceable indexing ring rotationally fixedly mounted on the shaft, the indexing ring comprising an annular fin projecting into a light barrier.

9. A microtome comprising:
   a drive device, including a shaft, for producing a movement between a knife and an object holder;
   a handle for manual actuation of the driving device;
   a blocking mechanism for locking the drive device, wherein the handle comprises switching means for actuation of the blocking mechanism, and the blocking mechanism further comprises,
   an electromagnet, arranged in the microtome, and
   a disk rotationally fixedly mounted on the shaft of the drive device.

10. The microtome as claimed in claim 9, wherein the disk comprises a gear ring, and said blocking mechanism includes a blocking lever, pivotally arranged on a housing frame of the microtome for engagement with said gear ring responsive to the electromagnet.

11. The microtome as claimed in claim 9, wherein the electromagnet is arranged on a housing frame, comprises an annular electro-permanent magnet, and is arranged opposite the disk, which is mounted axially displaceably on the shaft.

12. The microtome as claimed in claim 11, wherein the electromagnet and the disk comprise toothing.

13. The microtome as claimed in claim 9, further comprising a control device electrically connected to the electromagnet and to a sensor.

14. The microtome as claimed in claim 13, wherein the sensor comprises a proximity sensor for detecting the position of an axially displaceable indexing ring rotationally fixedly mounted on the shaft.

15. The microtome as claimed in claim 13, wherein the sensor comprises a light barrier for detecting the position of an axially displaceable indexing ring rotationally fixedly mounted on the shaft, the indexing ring comprising an annular fin projecting into a light barrier.

16. A microtome comprising:
   a drive device for producing a movement between a knife and an object holder;
   a handle for manual actuation of the drive device; and
   a blocking mechanism for locking the drive device, wherein the handle comprises switching means for actuation of the blocking mechanism, said switching means comprising:
   a grip with a rotationally movable gripping piece,
   a switch arranged in the gripping piece, and
   a thrust pin under spring force, arranged inside the grip, the thrust pin being axially movable to actuate the blocking mechanism in response to the switch.

17. A microtome comprising:
   a drive device for producing a movement between a knife and an object holder;
   a handle for manual actuation of the drive device; and
   a blocking mechanism for locking the drive device, wherein the handle comprises switching means for actuation of the blocking mechanism, said switching means comprising:
   a grip with a rotationally movable gripping piece, and
   a switch arranged in the gripping piece, the switch being connected via electric leads and electric sliding contacts to a control device for actuating the blocking mechanism.

18. A microtome comprising:
   a housing frame;
   a drive device mounted in the housing frame for producing a movement between a knife and an object holder;
   a handle mounted on the housing frame for manual actuation of the drive device;
   a blocking mechanism for locking the drive device, said blocking mechanism including recesses in the housing frame adjacent the handle, wherein the handle comprises switching means for actuation of the blocking mechanism, wherein said switching means comprises:
   a grip with a rotationally movable gripping piece,
   a switch arranged in the gripping piece, and
   a thrust pin under a spring force, arranged inside the grip and being normally in engagement with one of said recesses, the thrust pin being axially movable in response to actuation of the switch to disengage from said recess.

* * * * *